(12) United States Patent
Hammarlund et al.

(10) Patent No.: US 6,223,745 B1
(45) Date of Patent: May 1, 2001

(54) METHOD AND A DEVICE FOR PRODUCING A FINE HOMOGENEOUS AEROSOL

(75) Inventors: Nils Hammarlund, Sollentuna; Leif Nilsson, Lidingö, both of (SE)

(73) Assignee: AGA Aktiebolag, Lidingo (SE)

( * ) Notice: Subject to any disclaimer, the term of this patent is extended or adjusted under 35 U.S.C. 154(b) by 0 days.

(21) Appl. No.: 09/284,515

(22) PCT Filed: Oct. 15, 1997

(86) PCT No.: PCT/SE97/01728
§ 371 Date: May 20, 1999
§ 102(e) Date: May 20, 1999

(87) PCT Pub. No.: WO98/16271
PCT Pub. Date: Apr. 23, 1998

(30) Foreign Application Priority Data
Oct. 16, 1996 (SE) .................................. 9603804

(51) Int. Cl.$^7$ .................................................. A61M 11/00
(52) U.S. Cl. ............................... 128/200.18; 128/200.14; 128/200.21
(58) Field of Search ................... 128/200.18, 200.14, 128/200.19, 200.21; 239/338

(56) References Cited

U.S. PATENT DOCUMENTS

| | | |
|---|---|---|
| 240,421 * | 4/1881 | Iske ................................ 128/200.21 |
| 3,097,645 | 7/1963 | Lester . |
| 3,744,722 * | 7/1973 | Burns .................................. 239/338 |
| 4,007,238 * | 2/1977 | Glenn .................................. 239/338 |
| 4,484,577 | 11/1984 | Sackner et al. . |
| 4,674,491 * | 6/1987 | Brugger et al. ................. 128/200.14 |
| 5,287,847 * | 2/1994 | Piper et al. ...................... 128/200.21 |

FOREIGN PATENT DOCUMENTS 0 641 570 A1   3/1995   (EP) .

OTHER PUBLICATIONS

Australian Patent Abstract, (11) AU–A1–63 005/80.

* cited by examiner

Primary Examiner—John G. Weiss
Assistant Examiner—V. Srivastava
(74) Attorney, Agent, or Firm—Pearne & Gordon LLP

(57) ABSTRACT

A nebulizer and method for forming a finely atomized aerosol are provided. A first aerosol is formed by passing a gas jet across the mouth of a liquid channel that communicates with a liquid reservoir. The first aerosol then strikes a stop surface and is converted into a second, more finely atomized aerosol. The second aerosol impacts a buffer plate. The larger liquid particles in the second aerosol strike the plate and are either broken up or returned to the liquid reservoir. The smaller particles follow a labyrinthine path through at least one slit-shaped passage in the buffer plate, in the process forming a third, final aerosol. Selection of the passage size allows control of the particle size distribution of the third, final aerosol.

20 Claims, 4 Drawing Sheets

METHOD AND A DEVICE FOR PRODUCING A FINE HOMOGENEOUS AEROSOL

The present invention relates to a method for producing a finely atomized aerosol, using a stream of gas which sucks liquid with it from the mouth of a channel, which communicates with a supply of liquid in a container, so as to form an aerosol, after which liquid particles in the resulting aerosol are broken up into smaller particles in a subsequent stage. The invention also relates to an arrangement used for implementing the method.

Arrangements for producing aerosols in accordance with the above are generally referred to as nebulizers and are available in various designs; see, for example, EP-0,191, 018, WO95/20411 and WO95/25556.

Nebulizers of this type can be used especially for producing aerosols for medical treatment, i.e. aerosols containing drugs. Such treatment is of great importance for treating asthma and chronic bronchitis, for example, since drugs in aerosol form which are inhaled directly deposit in the airways.

Nebulizers previously available on the market have generally been designed to be used with drugs which have a wide therapeutic dose range, i.e. it has been possible to allow the dosage to be varied within wide limits without serious consequences, e.g. traditional asthma medications. Thus, the demand for exact and reproducible dosage has not been so stringent, and previous nebulizer designs have shown great individual variations, even between apparently identical examples of the same product. Nor has any great importance been attached to the quantity of aerosol produced in relation to the tidal volume, or to the patient's physiological requirements to assimilate the dose of medication. Nor has loss of medication to the environment been regarded as any particular problem.

This situation has changed now that a number of very powerful and usually also very expensive drugs for aerosol therapy have been made available by the drugs companies. Some of these drugs are in powder form. For these types of drugs, completely different and stringent demands have been imposed on the dosing equipment. In addition, the authorities place demands on function and reliability. Attention has also been paid to loss of medicine to the environment.

BRIEF SUMMARY OF THE INVENTION

The main object of the present invention is to solve the abovementioned problems and to make available a method and an arrangement permitting reproducible and documentable production of a medical aerosol which is suitably formulated for the individual patient group and is in a correctly adjusted quantity. In addition, loss of drug to the environment is to be eliminated or minimized.

The equipment must also be easy for the patient to handle, since it is a precondition for good treatment results that the equipment be very easy to handle, even for a very sick patient. The equipment must also be able to be used for administering both medicine in liquid form and also in powder form after mixing with a liquid.

The abovementioned objects are achieved by means of a method of the type indicated in the first paragraph, which method is characterized, according to the present invention, in that the stream of gas is directed essentially at right angles to the axial extent of the liquid channel and so that at least some of this stream of gas passes across the mouth of the liquid channel and thereafter strikes a stop surface situated at a distance from the mouth, whereupon liquid particles in the resulting aerosol are broken up, with a more finely atomized, second aerosol being formed.

The combination of a gas jet passing across the mouth of the liquid channel and a stop plate downstream of the gas jet has been found to give a very finely atomized aerosol, in which, according to a preferred embodiment of the invention, the size distribution of the liquid particles can be adapted to requirements by using one or more slit-shaped passages whose sizes are determined on the basis of the desired size distribution of the liquid particles. The slit-shaped passages are in this case formed expediently between a deflector plate and a surrounding housing, with the deflector plate being arranged in such a way that it catches liquid particles in the second aerosol and returns these to the liquid in the container.

When producing an aerosol for inhalation, this aerosol is expediently produced continuously in a quantity which corresponds to, or is less than, the inspiratory volume of the patient who is to inhale the aerosol, with the aerosol formed between breaths being collected in a dosing bag which empties during the succeeding breath.

Other features of the method according to the invention and of an arrangement for use in implementing the method will become clear from the attached patent claims.

The invention will be described in greater detail below with reference to the attached drawings, which show some embodiments of the invention which have been chosen as examples.

DETAILED DESCRIPTION OF THE INVENTION

Figure 1:
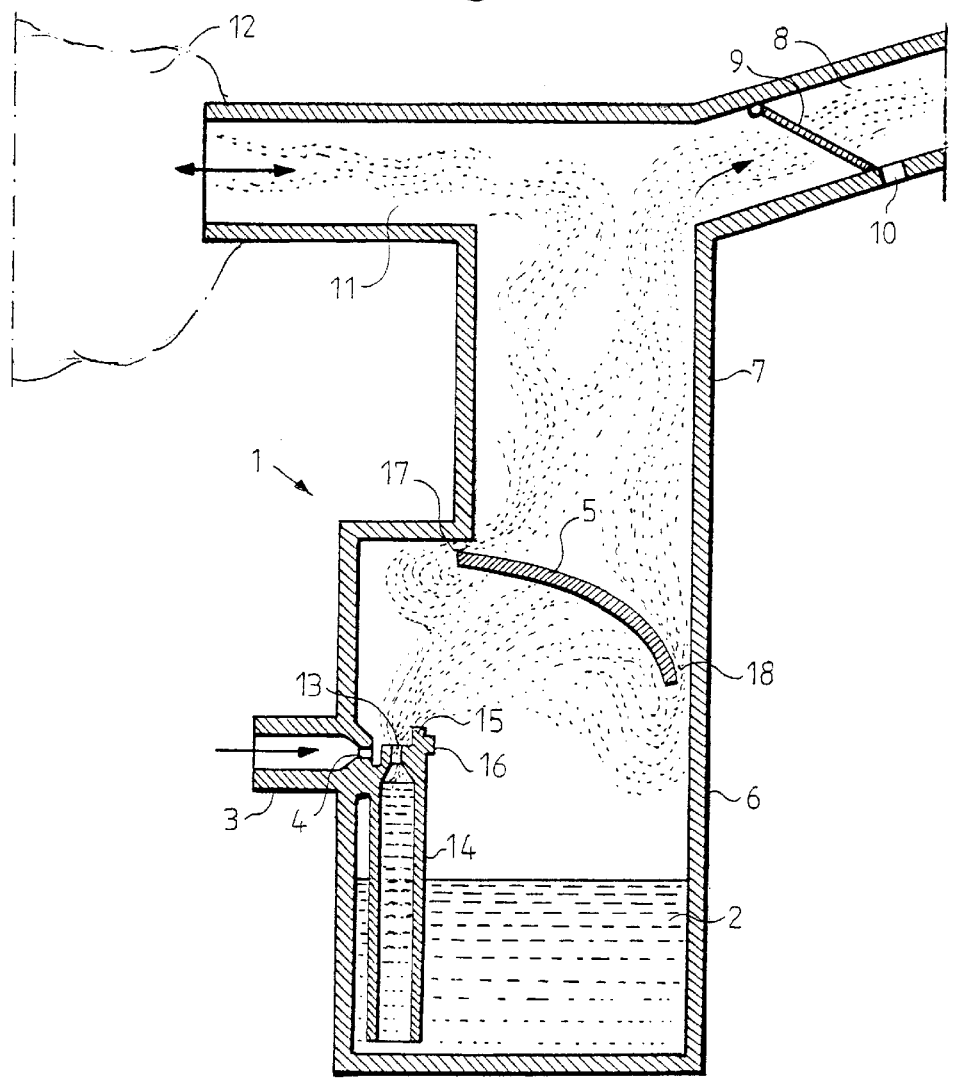
FIG. 1 illustrates, in cross-section, the basic structure of a nebulizer according to the present invention.
Figure 2:
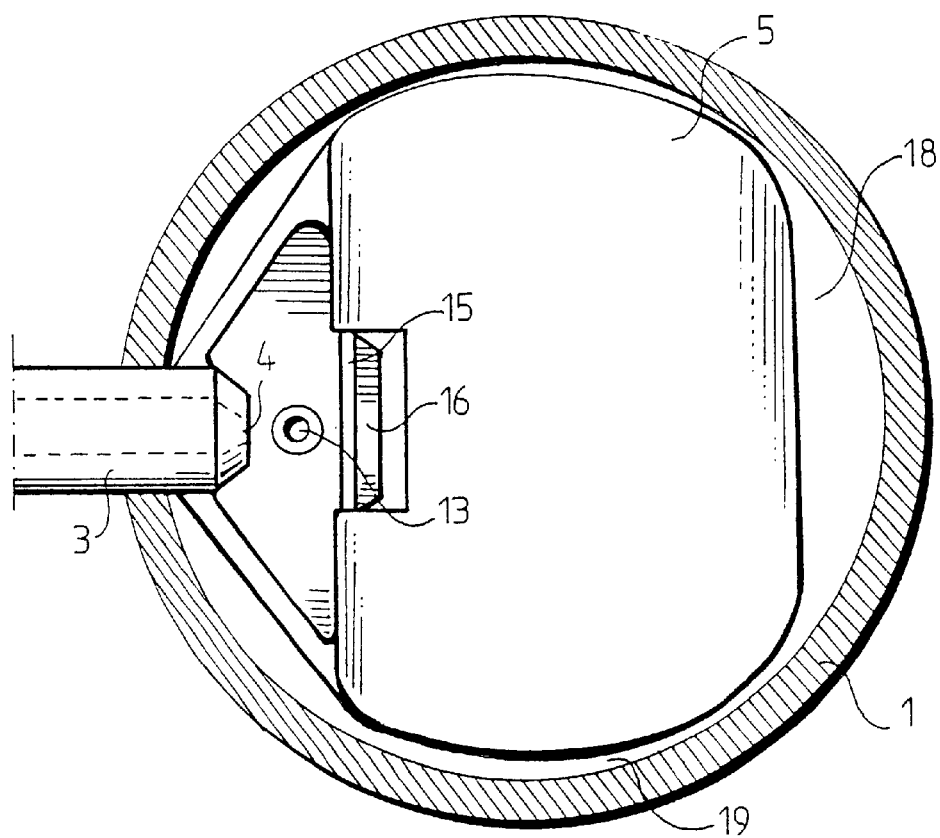
FIG. 2 is a cross-section through the nebulizer in FIG. 1, with a holder arrangement for the deflector plate also being shown.

In FIGS. 1 and 2, reference number 1 designates the housing of a nebulizer according to the invention, containing a supply 2 of a medical preparation in liquid form. The preparation can also be in powder form and be mixed with a liquid. Reference number 3 designates a gas inlet for a carrier gas, such as air or a gas mixture containing helium and/or neon and oxygen. The carrier gas is delivered at a pressure of the order of 1–10 bar, preferably about 5 bar. The flow is adapted by configuring the nozzle 4 to the patient's inspiratory volume per minute, which, for an adult with normal pulmonary function, is about 4.5 liters/minute.

Reference number 5 designates a curved deflector plate which essentially screens off the lower part 6 of the housing 1, containing the liquid magazine 2, from the upper part 7 of the housing, having an outlet 8 intended to be connected to a mouthpiece which the patient will breathe through. The outlet 8 is provided with a nonreturn valve 9 and one or more exhalation openings 10. The illustrated embodiment is also provided with an outlet 11 connected to a flexible dosing bag 12.

The function of the above-described arrangement is as follows. When the carrier gas is introduced, the nozzle 4 forms a gas jet which is directed essentially at right angles to the axial extent of a channel 14 which communicates with the liquid magazine 2. At least part of the gas jet passes, with expansion, closely across the mouth 13 of the channel 14. The gas jet will thus suck liquid particles with it in the form of an aerosol from the mouth 13 and will bring these into contact with a vertical stop surface 15. In the resulting aerosol, the larger liquid particles in particular strike the stop surface 15 and will be broken up, on contact with the latter, to form a more finely atomized, second aerosol, which rises upwards in the housing 1.

The distance from the centre of the mouth 13 to the nozzle 4 is expediently 1–3 mm, preferably about 2 mm. For a good suction effect, and in order to prevent the carrier gas from being forced downwards in the channel 14, the nozzle 4 is situated at a lower level than the mouth 13, the distance in the vertical direction between the centre line of the nozzle 4 and the mouth 13 being 0.1–1 mm, preferably about 0.3 mm. For an increased venturi effect, a plate can be arranged to extend from the top side of the nozzle 4 and forwards across the mouth 13 of the liquid channel. The plate expediently slopes slightly upwards in the direction of the said mouth.

The stop surface 15, designed in the form of a plate, has sharp upper edges, and is provided on its rear surface, as viewed in the direction of flow of the gas jet, with an outwardly protruding plateau 16 having a length of 1–10 mm, preferably about 2 mm. The plateau has the effect, inter alia, that an underpressure is created on the rear side of the stop plate 15, and this imparts a downward force to the aerosol stream, which prevents this from being directed too high. The plateau can also be located level with the upper edge of the plate 15. The front surface of the plate can be provided with a screen arranged at its upper edge and/or with a recess where the gas jet hits the surface.

The aerosol finely atomized by the plate 15 passes upwards in the housing 1, its flow movements being influenced by the deflector plate 5. Especially the larger particles in the aerosol hit the plate and run down along the latter and are returned to the liquid magazine 2.

The deflector plate 5, which is located 10–40 mm, expediently about 25 mm, above the mouth 13, is designed and arranged such that a slit-shaped passage is formed between the housing 1 and the front and rear edges, respectively, of the plate. These passages 17 and 18, respectively, can have a height or width of 0.5–4 mm, preferably about 1 mm, and a length of 5–20 mm, preferably about 15 mm. In addition, there can be a narrow slit 19 between the plate 5 and the housing 1 along the side edges of the plate, see FIG. 2.

The plate 5, together with the slit-shaped passages 17, 18, will act on the flow characteristics of the aerosol and will make it possible in advance, by means of suitable dimensioning of the said passages, inter alia as a function of the pressure of the delivered gas, to achieve the desired size distribution of the liquid particles in the final aerosol. The slits 17 and 18 form labyrinthine passages which require changes in the direction of the liquid particles in the aerosol in order for them to pass. As a function of the flow velocity, which at constant pressure is affected by the slit width, inter alia, liquid particles of certain sizes will strike against the walls and either be broken up or returned to the liquid magazine 2. The passage 18 also allows liquid which condenses in the upper part of the housing 1 to return to the liquid magazine.

Using a deflector plate 5, it is thus possible, as a function of the dimensions and design of, above all, the slits 17 and 18, to act on the size distribution of the particles in the final aerosol and thus to adapt this aerosol to the requirements of the patient groups, the drug in question, and the site in the lungs where deposition is desired.

After passing the deflector plate 5, the aerosol reaches the outlet 8 and is inhaled by the patient, with the nonreturn valve 9 opening. On exhaling, the nonreturn valve closes, whereupon the exhaled air has to pass out through the opening 10. The patient is thus able to inhale and exhale completely normally without removing from his/her mouth a mouthpiece attached to the inlet 8. The area of the exhalation opening 10 is adapted to offer a certain resistance to exhalation, which means that the patient's airways are spread open, and breathing and deposition of the medical aerosol are improved. If the drug is of a type which requires that even small leakages of medicine to the environment have to be prevented, then a medical filter can be arranged in connection with the exhalation opening 10.

In the embodiment shown, the aerosol formation continues even during the exhalation phase, for which reason the housing 1 has been provided with an outlet opening 11 to which a flexible dosing bag 12 is connected. This dosing bag will fill as the patient exhales and will empty during the succeeding inhalation. The stream of gas to the arrangement, and thus the production of aerosol, is adapted such that it corresponds to, or is slightly less than, the patient's inspiratory volume, and any additional air will be inhaled via the opening 10.

One of the advantages achieved by adapting the quantity of aerosol produced per unit time and the size of the dosing bag to the inspiratory volume is the following. It is greatly desired that the dose of medicine supplied on each inhalation will be deposited in the lungs, since that aerosol which reaches the upper airways and the oral cavity and throat deposits the drug at an undesired site, where it has no appreciable impact or may cause side effects. Alternatively, it will be exhaled to no benefit and may create problems for the environment. By means of the dosing bag having a defined volume which is less than the inspiratory volume, the last-inhaled volume in each respiration will consist essentially of pure air, which is drawn in via the opening 10, together with a small quantity of aerosol which is produced during the actual inhalation. This diluted gas volume will settle as a cushion in the upper airways and thereby prevents the drug from being deposited at an undesired site. By adapting the volume of the dosing bag and the quantity of aerosol produced, it is thus possible to dictate where in the lungs a drug will be deposited.

In some cases the aim may be to concentrate the deposition of the drug in the peripheral regions of the lungs. This can be done by producing an aerosol which is of considerably smaller volume than the inspiratory volume and which is inhaled first during respiration. The medicine included therein is thus deposited essentially in the peripheral regions of the lungs, while the rest of the lungs and airways are filled essentially with pure air, which is inhaled after the dose of medicine.

Figure 3:
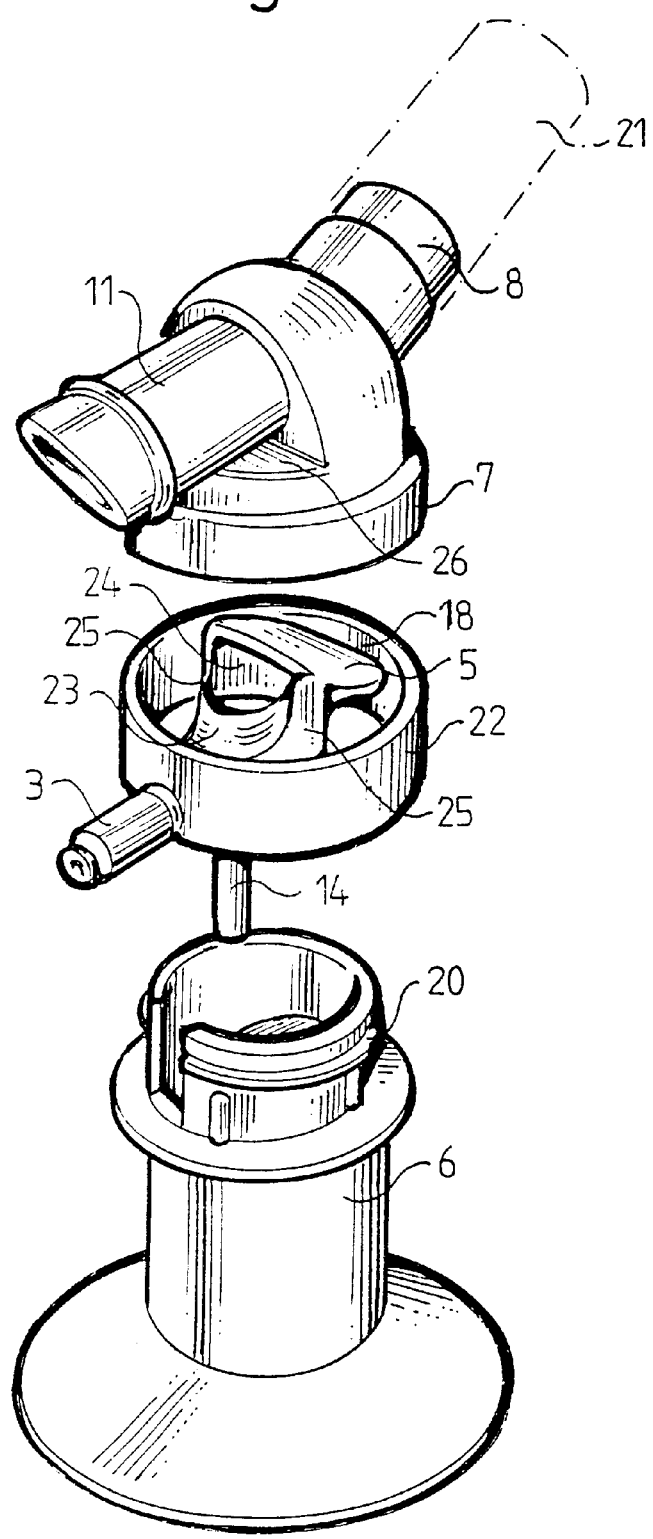
FIG. 3 is an exploded view of a preferred embodiment of a nebulizer according to the invention.
Figure 4:
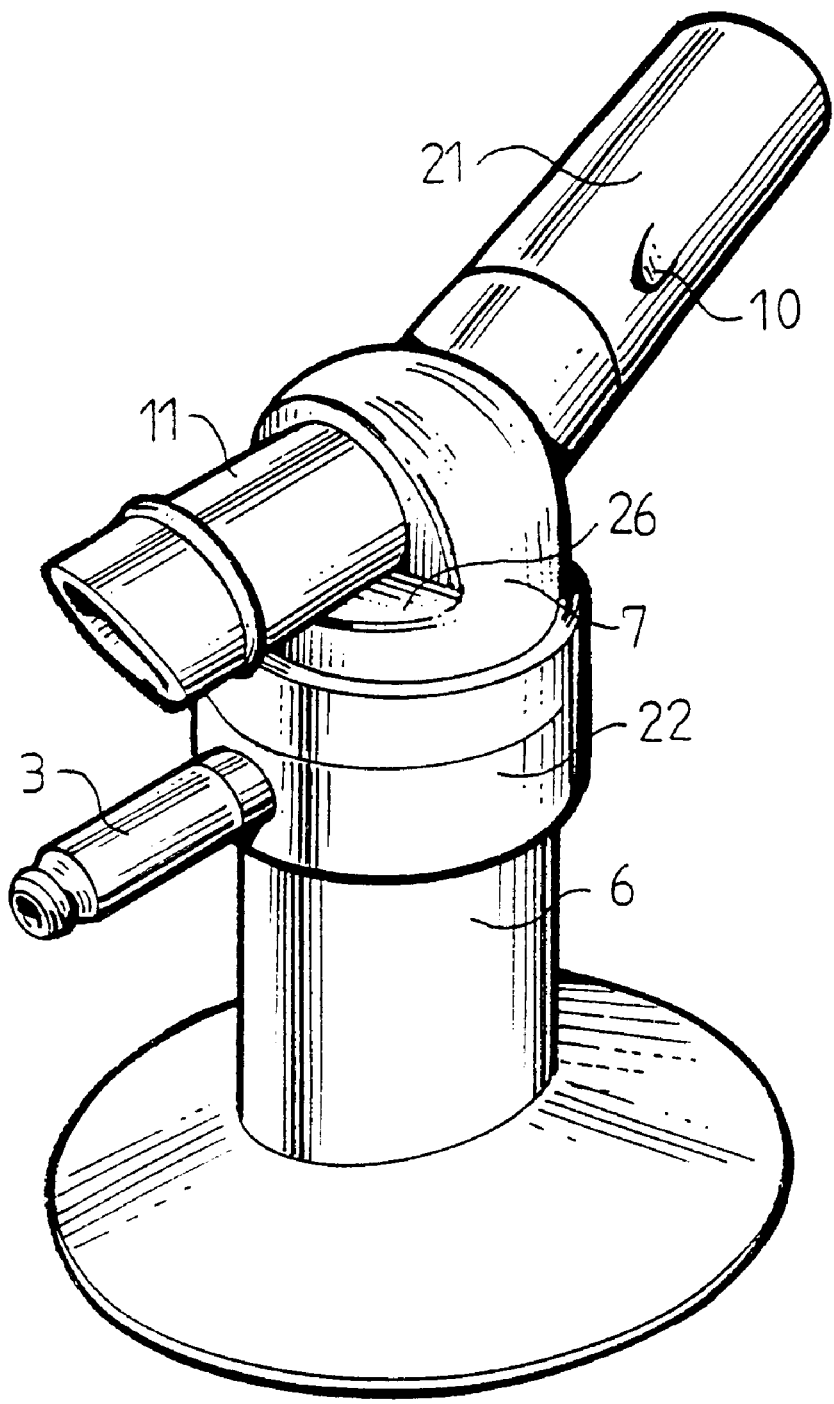
FIG. 4 shows the nebulizer according to FIG. 3 in the assembled state.

FIGS. 3 and 4 show a preferred embodiment of a nebulizer according to the invention which works according to the principle which has been described in conjunction with FIGS. 1 and 2. The same reference numbers have been used for those components in FIGS. 3 and 4 which correspond to components in FIGS. 1 and 2.

The exploded view in FIG. 3 shows that the nebulizer is made up of a lower part 6, which contains a liquid magazine and is provided with an outer thread 20 for cooperation with a corresponding inner thread on the upper part 7. A suction mouthpiece 21 equipped with a nonreturn valve can be connected to the part 7. This suction mouthpiece 21 expediently has a round shape in order to prevent the patient from unintentionally closing his/her mouth and in this way drawing the aerosol through the teeth. The part 7 moreover carries the outlet 11 which is intended to be connected to a dosing bag (not shown).

Reference number 22 designates an intermediate unit which carries the gas attachment 3, which leads to the nozzle 4, in FIG. 1, located on the rear side of a sloping wall 23. The channel 14 designed in the shape of a pipe protrudes down under the part 22 and has its upper mouth 13, in FIG. 1, located alongside the gas nozzle. The wall 23 collects the aerosol after this has hit the stop plate 15, in FIG. 1, and it conveys some of this aerosol up through an opening 24, so that it can be deflected and can pass to the top side of the deflection plate 5. The remainder passes along the underside of the plate towards the slit 18. Some also passes through the slit 19.

When the parts are joined together, as is shown in FIG. 4, that portion of the part 6 provided with the thread 20 will protrude upwards into and delimit the free space around the deflection plate 5 and the support legs 25 thereof.

When the upper part 7 is threaded firmly onto the lower part 6, clamping the middle part 22 between them, a horizontal portion 26 of the part 7 will be situated immediately above the plate 5 and, together with this, will form the slit 17, in FIG. 1, with predetermined dimensions. The plate 5 is also dimensioned in such a way that a slit 18 according to FIG. 1 is formed between the rear edge of the plate and the circular wall of the part 22, and a slit 19 is formed between the side edges of the plate 5 and the circular wall.

The above-described embodiment has the great advantage that all the critical parts of the nebulizer which may need to be varied to achieve the desired function are found in one exchangeable part 22 designed as one unit. The nebulizer can thus be used with different configurations of the components in part 22 in order, inter alia, to produce the size distribution, desired in the case in question, of the liquid particles in the resulting aerosol.

The practical production of a nebulizer according to the present invention may, however, be varied in several respects within the scope of the patent claims. Thus, for example, the shape of the deflector plate 5 can be varied. For example, instead of being dome-shaped, it can consist of an inclined, flat plate. It can also be designed in such a way that there is a slit only at one edge, expediently the front edge. The arrangement can also be used without a dosing bag, in which case the outlet 11 is omitted. When the nebulizer is to be used for drugs of high viscosity, the nozzle 13 can be designed in the shape of a shallow dish.

What is claimed is:

1. Method for producing a finely atomized aerosol, using a stream of gas which sucks liquid with it from a mouth of a liquid channel, which communicates with a supply of liquid in a container, so as to form a first aerosol, after which particles of liquid in the first aerosol are broken up into smaller particles in a subsequent stage, characterized by the steps of directing the stream of gas essentially at right angles to the axial extent of the liquid channel to pass at least some of the stream of gas across the mouth of the liquid channel to form the first aerosol and thereafter impacting the first aerosol against a stop surface situated at a distance from the mouth to break up liquid particles in the first aerosol to form a second aerosol, the second aerosol being more finely atomized, impacting substantially all of the second aerosol against a deflector plate to return a portion of the liquid in the second aerosol to the liquid in the container and force the remaining portion of the second aerosol to follow a labyrinthine path changing direction and passing through one or more narrow slit-shaped passages to form a third aerosol having the desired size distribution of liquid particles.

2. Method according to claim 1 for producing an aerosol for inhalation, characterized in that the aerosol is produced continuously in a quantity which corresponds to, or is slightly less than, the inspiratory volume of the patient who is to inhale it, and in that the aerosol which is formed between breaths is collected in a dosing bag, which empties during the succeeding breath.

3. Method according to claim 2 characterized in that an aerosol of considerably smaller volume than the inspiratory volume is produced so that medicine included in the aerosol is essentially deposited in the peripheral regions of the lungs, while the rest of the lungs and the airways are filled principally with air.

4. Method according to claim 1, including the steps of passing the second aerosol along a flow path having a cross-sectional area, the deflector plate extending across and blocking the flow path except for the one or more narrow slit-shaped passages.

5. Arrangement for producing a finely atomized aerosol, using a stream of gas which sucks liquid with it from the mouth (13) of a liquid channel (14), which communicates with a supply (2) of liquid in a container (6), so as to form a first aerosol, which arrangement comprises a member (15) which, in a second stage, breaks up liquid particles in the first aerosol into smaller particles, characterized in that the arrangement comprises members (3, 4) for directing the stream of gas essentially at right angles to the axial extent of the liquid channel (14) and so that at least some of this stream of gas passes across the mouth (13) of the liquid channel, and a stop surface (15) located at a distance from the mouth, and downstream thereof in the direction of the jet of gas, whereupon liquid particles in the first aerosol are broken up, with a second aerosol being formed upon contact with the stop surface, said second aerosol being more finely atomized, the arrangement further comprising a deflector plate (5) for catching liquid particles in the second aerosol and returning these to the liquid (2) in the container, said deflector plate placed so that substantially all of the second aerosol impacts against the plate, said deflector plate together with a surrounding housing (1) forming at least one narrow slit-shaped passage for the remainder of the second aerosol, forcing the remaining portion of the second aerosol to follow a labyrinthine path, changing direction and passing through the at least one narrow slit-shaped passage to form a third aerosol having the desired size distribution of liquid particles.

6. Arrangement according to claim 5, characterized in that the deflector plate (5) is curved and is located at a distance above the mouth (13) of the liquid channel, and in that a slit-shaped passage (17, 18) is formed along the front and rear edges of the plate (5) as viewed in the direction of the stream of gas across the mouth of the liquid channel.

7. Arrangement according to claim 5 or 6, characterized in that the slit-shaped passages (17, 18) have a width or height of about 0.5–4 mm, and a length of about 5–20 mm.

8. Arrangement according to claim 5, characterized in that the stream of gas is delivered via a gas inlet (3, 4) which opens out at a lower level than the mouth (13) of the liquid channel, expediently about 0.1–1 mm below the mouth.

9. Arrangement according to claim 5, characterized in that the stop plate (15) is situated about 0.1–2 mm from the mouth (13) of the liquid channel.

10. Arrangement according to claim 5 characterized in that the stop plate (15) has sharp upper edges, and a plateau (16) projecting from the rear side and in the direction taken by the stream of gas.

11. Arrangement according to claim 10, characterized in that the plateau (16) is situated at a lower level than the upper edge surface of the plate (15) and extends about 1–10 mm, in the direction taken by the stream of gas.

12. Arrangement according to any claim 5 characterized in that it comprises a plate which extends across the gas inlet (4) and forwards across the mouth (13) of the liquid channel.

13. Arrangement according to claim 5, characterized in that the deflector plate (5) is part of an exchangeable unit, which also includes the liquid channel (14) and the members (3, 4) for directing the stream of gas, as well as the stop plate (15).

14. Arrangement according to claim 5, wherein said deflector plate has an area substantially greater than the area of the at least one slit-shaped passage.

15. Arrangement according to claim 5, wherein said housing provides a flow path having a transverse area through which said second aerosol flows and said deflector plate extends across substantially all of said transverse area of said flow path to prohibit flow of said second aerosol except through the at least one slit-shaped passage.

16. Arrangement according to claim 5, wherein said second aerosol passes axially along a flow path provided by said housing and said deflector plate is transversely disposed at an inclined angle across said flow path.

17. Arrangement according to claim 5, wherein said deflector plate cooperates with said housing to form a second slit-shaped passage spaced apart from the first mentioned at least one slit-shaped passage.

18. Arrangement according to claim 5, wherein the at least one slit-shaped passage has a width to length ratio in the range of 1:40 to 4:5.

19. Arrangement according to claim 5, wherein the at least one slit-shaped passage has a width to length ratio of 1:15.

20. Arrangement according to claim 5, wherein the second stage member has a substantially planar surface impacted by the first aerosol.

* * * * *